US008003690B2

(12) United States Patent  
Vergnault et al.

(10) Patent No.: US 8,003,690 B2
(45) Date of Patent: Aug. 23, 2011

(54) TOPICAL NANOPARTICULATE SPIRONOLACTONE FORMULATION

(75) Inventors: Guy Vergnault, Kembs Loechle (FR); Pascal Grenier, Kappelen (FR); Alain Nhamias, Bartenheim (FR); Dieter Scherer, Muttenz (CH); Petra Beck, Muttenz (CH); Patricia Cancade, Saint-Louis (FR)

(73) Assignee: Jagotec AG, Muttenz (CH)

( * ) Notice: Subject to any disclaimer, the term of this patent is extended or adjusted under 35 U.S.C. 154(b) by 1521 days.

(21) Appl. No.: 10/538,344

(22) PCT Filed: Dec. 13, 2002

(86) PCT No.: PCT/GB02/05680

§ 371 (c)(1),
(2), (4) Date: Jun. 9, 2005

(87) PCT Pub. No.: WO2004/054549

PCT Pub. Date: Jul. 1, 2004

(65) Prior Publication Data

US 2006/0067892 A1    Mar. 30, 2006

(51) Int. Cl.
*A61K 31/343* (2006.01)
(52) U.S. Cl. ........................................ 514/462
(58) Field of Classification Search ............... None
See application file for complete search history.

(56) References Cited

U.S. PATENT DOCUMENTS

| | | | |
|---|---|---|---|
| 4,011,316 A | 3/1977 | Barton | |
| 4,801,455 A | 1/1989 | List et al. | |
| 4,837,211 A | 6/1989 | Olsen et al. | |
| 4,895,726 A | 1/1990 | Curtet et al. | |
| 5,091,188 A | 2/1992 | Haynes | 424/450 |
| 5,145,684 A | 9/1992 | Liversidge et al. | 424/489 |
| 5,506,222 A * | 4/1996 | Stefano et al. | 514/173 |
| 5,510,118 A | 4/1996 | Bosch et al. | |
| 5,858,410 A | 1/1999 | Muller et al. | 424/489 |
| 5,880,148 A | 3/1999 | Edgar et al. | |
| 5,891,469 A | 4/1999 | Amselem | |
| 5,891,845 A | 4/1999 | Myers | |
| 6,013,637 A * | 1/2000 | Klein et al. | 514/43 |
| 6,028,054 A | 2/2000 | Benet et al. | |
| 6,121,234 A | 9/2000 | Benet et al. | |
| 6,180,138 B1 | 1/2001 | Engh et al. | |
| 6,193,985 B1 | 2/2001 | Sonne | |
| 6,228,383 B1 * | 5/2001 | Hansen et al. | 424/407 |
| 6,294,192 B1 | 9/2001 | Patel et al. | |
| 2002/0006919 A1 | 1/2002 | Thosar et al. | |
| 2002/0136775 A1 | 9/2002 | Thosar et al. | |
| 2008/0069886 A1 | 3/2008 | Vergnault et al. | |

FOREIGN PATENT DOCUMENTS

| | | |
|---|---|---|
| EP | 0 256 285 | 2/1988 |
| EP | 0 410 348 A1 | 1/1991 |
| EP | 0 603 405 A1 | 6/1994 |
| JP | 03095120 A | 4/1991 |
| JP | 04503800 | 7/1992 |
| JP | 04295420 A | 10/1992 |
| JP | 5331066 A | 12/1993 |
| WO | WO 83/00294 | 2/1983 |
| WO | WO 87/02582 | 5/1987 |
| WO | WO 96/25918 | 8/1996 |
| WO | WO 98/30360 | 7/1998 |
| WO | WO 98/31360 | 7/1998 |
| WO | WO 98/31361 | 7/1998 |
| WO | WO 99/21534 | 5/1999 |
| WO | WO 99/29300 | 6/1999 |
| WO | WO 99/40904 | 8/1999 |
| WO | WO 99/65469 | 12/1999 |
| WO | WO 00/30616 | 6/2000 |
| WO | WO 00/51572 | 9/2000 |
| WO | WO 01/37808 | 5/2001 |
| WO | WO 01/49262 | 7/2001 |
| WO | WO 02/102391 | * 12/2002 |

OTHER PUBLICATIONS

Schefer-Korting, et al., "Delivery of Lipophillic Compounds with Lipid Nanoparticles—Applications in Dermatics and for Transdermal Therapy," in "Liposphieres in Drug Targets and Delivery," CRC Press (2005) Claudio Nastruzzi, Editor.*
Mehnert, et al., Advanced Drug Delivery Reviews, 47:165-196 (2001).*
Muhlen, et al, European Journal of Pharmaceutics and Biopharmaceutics, 45:149-155 (1998).*
Drug Bank, Spironolactone entry accessed Jan. 14, 2008.*
Ralph Lane, "Overview of Fats and Oils," (2004) accessed on Jan. 22, 2008 at http://ches.ua.edu/departments/nhm/faculty/lane/nhm454/McWCh11&12fats.pdf.*
Kirk-Othmer Encyclopedia of Chemical Technology (2007), "Sodium Docusate" in "Gastrointestinal Agents," p. 16, second full paragraph. Accessed Feb. 9, 2008.*
2.4 Physical properties of low polar emulsifiers. edited by J. Sjoblom, (1992), Kluwer Academic Publishers, pp. 64-65.*
Muller, et al. European Journal of Pharmaceutics and Biopharmaceuticals, (2000), vol. 50 pp. 161-177.*
Prostate Cancer [online], retrieved on Aug. 5, 2009. Retrieved online from URL: http://www.nlm.nih.gov/medlineplus/prostatecancer.html.*
da Silveira et al., "Influence of solubility and partition coefficient on the loading of combined poly(isobutylcyanoacrylate) and hydroxypropyl-β-cyclodextrin nanoparticles by steroids", *S.T.P. Pharma Sci.*, 10(4):309-314 (2000).
El-Shabouri, M.H., "Nanoparticles for improving the dissolution and oral bioavailability of spironolactone, a poorly-soluble drug", *S.T.P. Pharma Sci.*, 12(2):97-101 (2002).
Duchene et al. (1999). J. Controlled Release 62:263-268.

* cited by examiner

*Primary Examiner* — Shawquia Young
(74) *Attorney, Agent, or Firm* — Mintz Levin Cohn Ferris Glovsky and Popeo, P.C.; David E. Johnson, Esq.; Muriel Liberto, Esq.

(57) ABSTRACT

The invention relates to a topical nanoparticulate spironolactone formulation comprising nanoparticles having a mean diameter, measured by a photon correlation spectroscopy, in the range of from about 300 nm to about 900 nm. The nanoparticles are incorporated into a crystalline network system comprising a dispersion of solid crystals of polar lipids, said lipids exposing their hydrophilic side outwards and their hydrophobic side inwards towards the spironolactone nanoparticles.

20 Claims, 7 Drawing Sheets

TOPICAL NANOPARTICULATE SPIRONOLACTONE FORMULATION

RELATED APPLICATIONS

Figure 1:
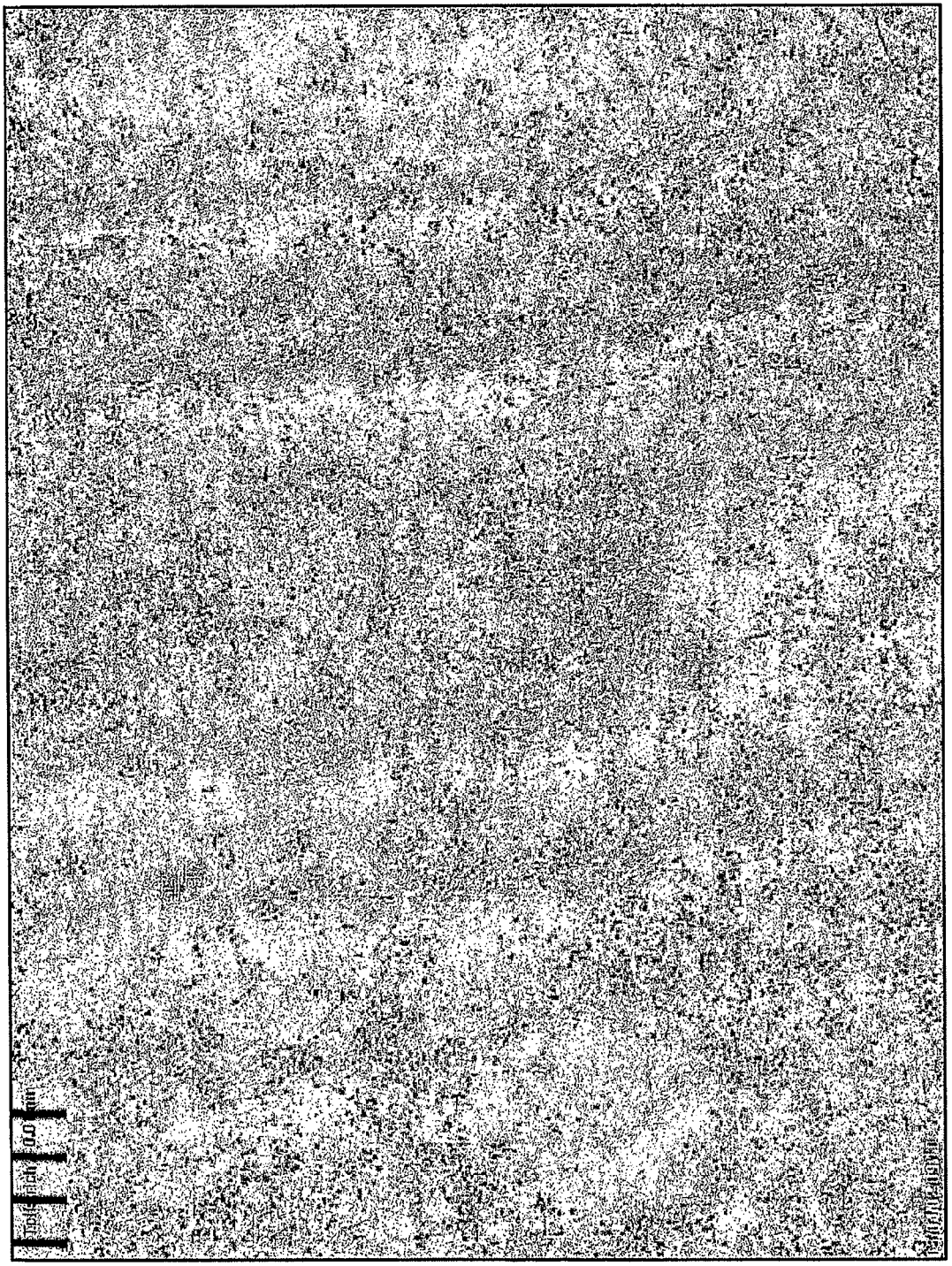

This application is a is a national stage application, filed under 35 U.S.C. §371, of International Application No. PCT/GB02/05680, filed on Dec. 13, 2002.

The present invention relates to the use of spironolactone in the form of nanoparticles in the topical treatment of a condition responding to anti-androgens. Such conditions include acne, hirsutism, androgenic alopecia or rosacea.

Spironolactone is known as an aldosterone inhibitor having utility as a potassium sparing diuretic. It is commercially available as e.g. aldactone and may be employed e.g. in the treatment of congestive heart failure. Spironolactone has extremely low solubility in water, viz: 2.8 mg/100 ml. This low solubility can adversely affect absorption of the drug substance in vivo, leading to poor bioavailability. Consequently higher amounts of the drug substance are required to achieve the desired blood levels. The poor solubility of spironolactone also restricts the options available for formulating the drug substance.

Other pharmaceutical applications make use of the anti-androgenic effects of Spironolactone for the treatment of a variety of skin disorders such as acne, hirsutism, androgenic alopecia and rosacea. Topical administration for these disorders would be the preferred route due to the greatly reduced systemic side effects. However, again it is the poor solubility of the drug, which limits the development of efficacious and aesthetically acceptable topical formulations.

Following oral administration, the absorption of drugs from the intestine is mainly dependent on their solubility in the intestinal fluids and their intestinal permeability. Poorly soluble drugs generally have low dissolution rates and exhibit only a small concentration gradient across the intestinal mucosa, which can result in low and unreliable levels of absorption. Drug substances which have low solubility also suffer from disadvantages in respect of other routes of administration, for example, topically.

Significant efforts have been directed to producing drug substances in the form of microparticles and nanoparticles. However, preparation of such small particles is not a trivial matter and can give rise to further difficulties both in relation to technical aspects of the process and in obtaining a satisfactory product. Thus for example there can be difficulties, especially on a manufacturing scale in obtaining a consistent and narrow particle size range. Furthermore, it is necessary to obtain stable products, e.g. nanosuspensions, but microparticles and nanoparticles have a tendency to aggregate and flocculate, which has adverse consequences for the stability of the product A number of different approaches have been investigated for the preparation of microparticles and nanoparticles.

U.S. Pat. No. 5,091,188 describes a method for preparing injectable solutions of water-insoluble drugs, which comprises reducing the crystalline drug substance to dimensions in the range 50 nm to 10 µm, by sonication or other processes inducing high shear, in the presence of a phospholipid or other membrane-forming amphipathic lipid, whereby the drug microcrystals become coated with said lipid.

U.S. Pat. No 5,145,684 describes particles of crystalline drug substance having a non-cross linked surface modifier adsorbed on the surface and an effective average particle size of less than about 400 nm. These particles are said to be prepared by milling in the presence of grinding media, using for example a ball mill, an attrition mill, a vibratory mill or a media mill.

International Patent Application WO 96/14830 (U.S. Pat. No. 5,858,410) describes a drug carrier which comprises particles of a pure active compound which is insoluble or only sparingly soluble in water, which has an average diameter of 10 nm to 1,000 nm and the proportion of particles larger than 5 µm in the total population is less than 0.1%. Preparation of the particles, with or preferably without surfactant, by means of cavitation (e.g. using a piston-gap homogenizer) or by shearing and impact forces (i.e. the jet stream principle) is also described.

There is a need for a topical formulation of nanoparticulate spironolactone that overcomes the problems of formulating the drug for topical administration.

The applicants have now shown that for topical administration, the spironolactone in the form of nanoparticles can be successfully incorporated into a cream base consisting of a crystalline network of monoglycerides in water.

In a first aspect therefore the present invention provides a topical nanoparticulate spironolactone formulation comprising nanoparticles having a mean diameter, measured by photon correlation spectroscopy, in the range of from about 300 nm to about 900 nm, preferably 400 nm to 600 nm incorporated into a crystalline network system comprising a dispersion of solid crystals of polar lipids, said lipids exposing their hydrophilic side outwards and their hydrophobic side inwards towards the spironolactone nanoparticles.

The formulation is suitable for application to the skin for use in treating dermatological conditions known to be treatable with antiandrogens e.g. acne, androgenic alopecia, hirsutism and rosacea. Cream bases consisting of a crystalline network of monoglycerides are described in WO87/02582, WO82/03173 and WO93/20812. Examples of such crystalline networks of monoglycerides are known as Crystalip™.

The lipids may have a crystallisation temperature of between 20° C. and 100° C. Preferable lipid crystals are β-crystals from a monoglyceride of a fatty acid having a chain length of 12-18 carbon atoms or monoglycerol ethers having ether chains of the corresponding length or fatty acid esters of ascorbic acid with a fatty acid chain length of 12-18 carbon atoms or mixtures thereof. The fatty acids as well as the ethers may be saturated or unsaturated, preferably saturated ones.

The fatty acids may therefore include lauric acid ($C_{12}$), myristic acid ($C_{14}$), palmitic acid ($C_{16}$) or stearic acid ($C_{18}$), although $C_{13}$, $C_{15}$, or $C_{17}$ acids could also be used.

Preferable monoglycerides may be a 1- or 2-monoglyceride, preferably a 1-monolaurin, 1-monomyristin, 1-monopalmitin and 1-monostearin or a mixture of two or more of these such as a mixture of 1-monolaurin and 1-monomyristin. Examples of unsaturated monoglycerides are monopalmitolein, monoolein, monolinolein and monoliniolenin.

The composition consists essentially of a dispersion of the above lipid crystals in water or any other polar liquid or mixtures thereof having the ability to allow crystal formation. Examples of polar lipids for use in accordance with the invention are water, glycerol, propylene glycol and ethylene glycol or mixtures thereof, however other suitable polar lipids may also be used.

The spironolactone is protected within the network up to the time of use but upon application to the skin, the spironolactone comes into contact with the skin surface as a consequence of softening or melting of the crystalline structure of the shell.

Generally one would expect a noticeable increase in particle size on storage following the incorporation of very fine solid particles into a matrix which contains hydrophilic as well as lipophilic structures. Surprisingly, this did not happen and there was no noticeable crystal growth of Spironolactone over a seven month period. Furthermore, the cream has shown an increased flux rate in a membrane model with respect to a cream with non-nanoparticulate spironolactone.

As is well known in the pharmaceutical art, particle size may be measured by a variety of methods, which can give rise to apparently different reported particle sizes. Such methods include photon correlation spectroscopy (PCS) and laser diffraction. Furthermore the particle size may be reported as an average particle size (e.g. a number average, weight average or volume average particle size). In the present specification, unless indicated otherwise, the particle size will be quoted as a volume average particle size. Thus for example, a $D_{50}$ of 500 nm indicates that 50% by volume of the particles have a diameter of less than 500 nm. Alternatively it can be stated that the particles having a diameter of less than 500 nm occupy 50% of the total volume occupied by the total number of particles.

When the particle size of spironolactone according to the present invention is measured by laser diffraction the $D_{50}$ is in the range 350-750 nm and the $D_{99}$ is in the range 500-900 nm.

Nanosuspensions and nanoparticles comprising spironolactone according to the present invention preferably incorporate a stabiliser to prevent aggregation of the nanoparticles. Such stabilisers, which are well known in the art, are described in more detail hereinafter.

In this specification nanoparticles comprising spironolactone and nanosuspensions comprising spironolactone according to the present invention will be referred to as nanoparticulate spironolactone. It should be appreciated that this term also includes nanoparticles and nanosuspensions comprising spironolactone in association with a stabiliser.

Nanoparticulate spironolactone according to the invention, may be prepared by any known method for the preparation of nanoparticles, in particular by high pressure homogenisation.

The nanoparticulate spironolactone may be prepared by subjecting a coarse dispersion of spironolactone to cavitation. Preferably the nanoparticles are prepared using a high pressure piston-gap homogeniser. The nanoparticles may be associated with a stabiliser. Such stabilisers, which are well known in the art, are described in more detail hereinafter.

For the preparation of nanoparticles it is preferred that the spironolactone starting material be utilised in the form of coarse particles, preferably having a particle size of less than about 100 μm. If necessary, the particle size of the spironolactone may be reduced to this level by conventional means, such as milling. The coarse particles of spironolactone are preferably dispersed in a liquid medium comprising a solvent in which the drug substance is essentially insoluble. In the case of spironolactone the liquid medium preferably comprises an aqueous solvent and most preferably consists essentially of water. The concentration of spironolactone in the said dispersion of coarse particles may be in the range 0.1 to 50%. The coarse dispersion may then be utilised in any known method for obtaining nanoparticles.

A preferred method is high pressure homogenization, wherein particle size is reduced mainly by cavitation. This is most preferably achieved using a high-pressure piston-gap homogeniser. In this method, the dispersion of coarse particles is forced at a high flow rate through a gap which is approximately 25 μm wide. The static pressure exerted on the liquid falls below the vapour pressure of the liquid. The liquid therefore boils, resulting in the formation of gas bubbles within the area of the gap. However, once the liquid exits from the gap, normal pressure prevails and the gas bubbles collapse. The powerful implosion forces which result are strong enough to break up the coarse particles of drug substance, resulting in the formation of nanoparticles.

High pressure homogenisation may be carried out at a pressure in the range 100 to 3000 bar, preferably 1000 to 2000 bar ($10^7$ to $3 \times 10^8$ Pa, preferably $10^8$ to $2 \times 10^8$ Pa) and at a temperature in the range 0 to 50° C., preferably 10 to 20° C., e.g. around 15° C. The homogenisation may be carried out in a series of cycles until the desired particle size is obtained, or as a continuous process, e.g. over a period of 2-30 hours, preferably 2-10 hours.

Nanosuspensions of spironolactone according to the present invention preferably incorporate a stabiliser to prevent aggregation of the nanoparticles. Said stabiliser may be introduced at any suitable stage during the manufacture of the nanosuspension. Thus for example, surfactant may be added to the initial coarse dispersion prior to the formation of nanoparticles or after reduction of the particles size, e.g. by high pressure homogenization, has taken place. Alternatively a portion of the stabiliser may be added before and a portion after the step of particle size reduction. Preferably stabiliser is present in the coarse dispersion. The concentration of stabiliser, either in the coarse dispersion or the nanosuspension may be in the range 0 to 10%.

Stabilisers which may be employed in the preparation of nanosuspensions according to the present invention may be selected from conventional stabilisers, and may include compounds which are also described a surfactants and surface modifiers. Thus examples of stabiliser which may be employed include: polyoxyethylene sorbitan fatty acid esters, e.g. Tweens and Spans; polyoxyethylene stearates; polyoxyethylene alkyl esters; polyethylene glycols; block polymers and block copolymers such as poloxamers e.g Lutrol F68, and poloxamines; lecithins of various origin (e.g. egg-lecithin or soya-lecithin), chemically-modified lecithins (e.g. hydrated lecithin), as well as phospholipids and sphingolipids, sterols (e.g. cholesterin derivatives, as well as stigmasterin), esters and ethers of sugars or sugar alcohols with fatty acids or fatty alcohols (e.g. saccharose monostearate); ethoxylated mono- and diglycerides, ethoxylated lipids and lipoids, dicetyl phosphate, phosphatidyl glycerine, sodium cholate, sodium glycolcholate, sodium taurocholate; sodium citrate; cellulose ethers and cellulose esters (e.g. methyl cellulose, hydroxyethyl cellulose, hydroxypropyl cellulose, sodium carboxymethyl cellulose), polyvinyl derivatives such as polyvinyl alcohol, polyvinyl pyrrolidone, polyvinyl acetate, alginates, polyacrylates (e.g. carbopol), xanthanes; pectins, gelatin, casein, gum acacia, cholesterol, tragacanth, stearic acid, calcium stearate, glyceryl monostearate, dioctyl sodium sulfosuccinate (sodium docusate); sodium lauryl sulfate, sodium dodecyl sulphate, benzalkonium chloride, alkyl aryl polyether sulfonate, polyethylene glycols; colloidal silicon dioxide, magnesium aluminium silicate; and phosphates.

A preferred stabiliser is sodium docusate, which is commercially available as a 70% solution in propylene glycol, under the name Octowet. 70PG™ (sodium dioctyl sulfosuccinate).

It will be appreciated from the foregoing that the process is carried out in a liquid medium and hence the nanoparticulate spironolactone product is initially obtained in the form of a nanosuspension. If desired the liquid medium may be removed, e.g. by lyophilisation or spray drying to provide nanoparticulate spironolactone in solid form. It will be appreciated that where a stabiliser is present during the manufacture of a nanosuspension, the corresponding dried nanoparticulate product will be associated with said stabiliser.

Following preparation of the nanoparticulate spironolactone, the formulation according to the invention may be prepared as follows. The polar lipid is mixed with water and/or any other polar liquid (such as glycerol, ethylene glycol or propylene glycol) having the ability to form crystalline network structures from polar lipids. The mixture formed has a concentration of water and/or polar liquid, respectively, of 50-95 percent by weight. The mixture is heated to a temperature above the transition temperature of the lipid. The transition temperature is defined as the lowest temperature at which a particle of the lipid in contact with an excess of water or polar liquid absorbs water or polar liquid respectively and is converted into cylindrical or spherical crystalline structures having a strong birefringence. The mixture is maintained above the transition temperature with stirring until the conversion has taken place. The mixture is then cooled with continued stirring to ambient temperature or the desired temperature, so that solid crystalline networks are formed. It is during this cooling down, at a temperature of about 30 to 35° C. that the characteristic crystalline structure is formed.

The nanoparticulate spironolactone is dispersed in the mixture of polar lipid and water or polar liquid before or while the lipid is transformed into crystalline structures. To ensure that the nanoparticulate spironolactone is incorporated into the crystalline structure it must be added before the mixture is cooled below 30 to 35° C.

If the nanoparticulate spironolactone is added after the mixture has been cooled to below 30 to 35° C., a physical mixture is formed but it does not form part of the crystalline structure. The nanoparticulate spironolactone therefore does not benefit from protection from and prevention of re-crystallisation and particle size growth of the active component since crystal layers are not formed around the active particles.

Nanosuspensions as used in the present invention in the formation of the topical formulation do not however respond well to heating. During heating, agglomerates may be formed and the active component may go into solution at higher temperatures. This can lead to re-crystallisation during the cooling down period which can result in a considerable increase in particle size.

The applicants have however determined a formulation, process and temperature of incorporation in order to allow formation of the crystalline structure after the addition of the nanosuspension, while keeping the heat exposure of the nanosuspension to a minimum.

Topical nanoparticulate spironolactone formulations according to the present invention advantageously incorporate the active drug in the form of a nanosuspension, most preferably in aqueous solution. Pharmaceutical formulations according to the present invention may be prepared according to methods well known in the art.

Topical formulations according to the present invention may be provided as an ointment, cream, gel, liquid, spray or mousse. Aqueous preparations may contain the nanosuspension as such; non-aqueous preparations can alternatively comprise dried nanoparticles.

In a second aspect the present invention provides a topical nanoparticulate spironolactone formulation for use in the topical treatment of conditions known to be treatable with antiandrogens, e.g. acne, androgenic alopecia, hirsutism and rosacea.

In a third aspect, the invention provides the use of spironolactone nanosuspensions comprising nanoparticles having a mean diameter, measured by photon correlation spectroscopy, in the range of from about 300 nm to about 900 nm, preferably 400 nm to 600 nm in the manufacture of a medicament for the treatment of a condition responding to antiandrogens, such as acne, hirsutism, androgenic alopecia or rosacea. The medicament may be adapted for topical application. The nanoparticles may be incorporated into a cream base which may consist of a crystalline network of monoglycerides in water or other polar liquids.

This aspect of the invention extends to providing a method of treating a condition responding to anti androgens comprising administering nanoparticulate spironolactone formulation as defined above to a patient in need of such treatment. The condition may be acne, hirsutism, androgenic alopecia or rosacea.

In a fourth aspect, the invention provides preparations comprising crystalline network system of solid crystals of polar lipids, said lipids exposing their hydrophilic side outwards and their hydrophobic side inwards towards an incorporated substance for use in the topical treatment of acne. The crystalline network system of solid crystals of polar lipids have previously been referred to as microcapsules in WO 87/02582.

In a fifth aspect there is provided a process for the preparation of a topical nanoparticulate spironolactone formulation comprising nanoparticles having a mean diameter, measured by photon correlation spectroscopy, in the range of from 300 nm to about 900 nm, wherein the process comprises incorporation of a nanosuspension of spironolactone into an aqueous dispersion of solid crystals of polar lipids, said lipids exposing their hydrophilic side outwards and their hydrophobic side inwards towards the spironolactone nanoparticles.

The nanosuspension may be incorporated when the mixture has been cooled to between 60° C. and 35° C., more preferably 55° C. to 45° C., suitably 50° C. before the mixture reaches its crystallisation point. The temperature of the nanosuspension at incorporation is preferably equal to room temperature i.e. 20 to 25° C.

Preferred features for the second and subsequent aspects of the invention are as for the first aspect mutatis mutandis.

The invention will now be illustrated with reference to one or more of the following non-limiting examples and figures.

FIG. 1 relates to a microscope picture of nanoparticulate spironolactone according to the present invention immediately after it has been prepared. The scale relates to a distance between each bar of 0.01 mm.

Figure 2:
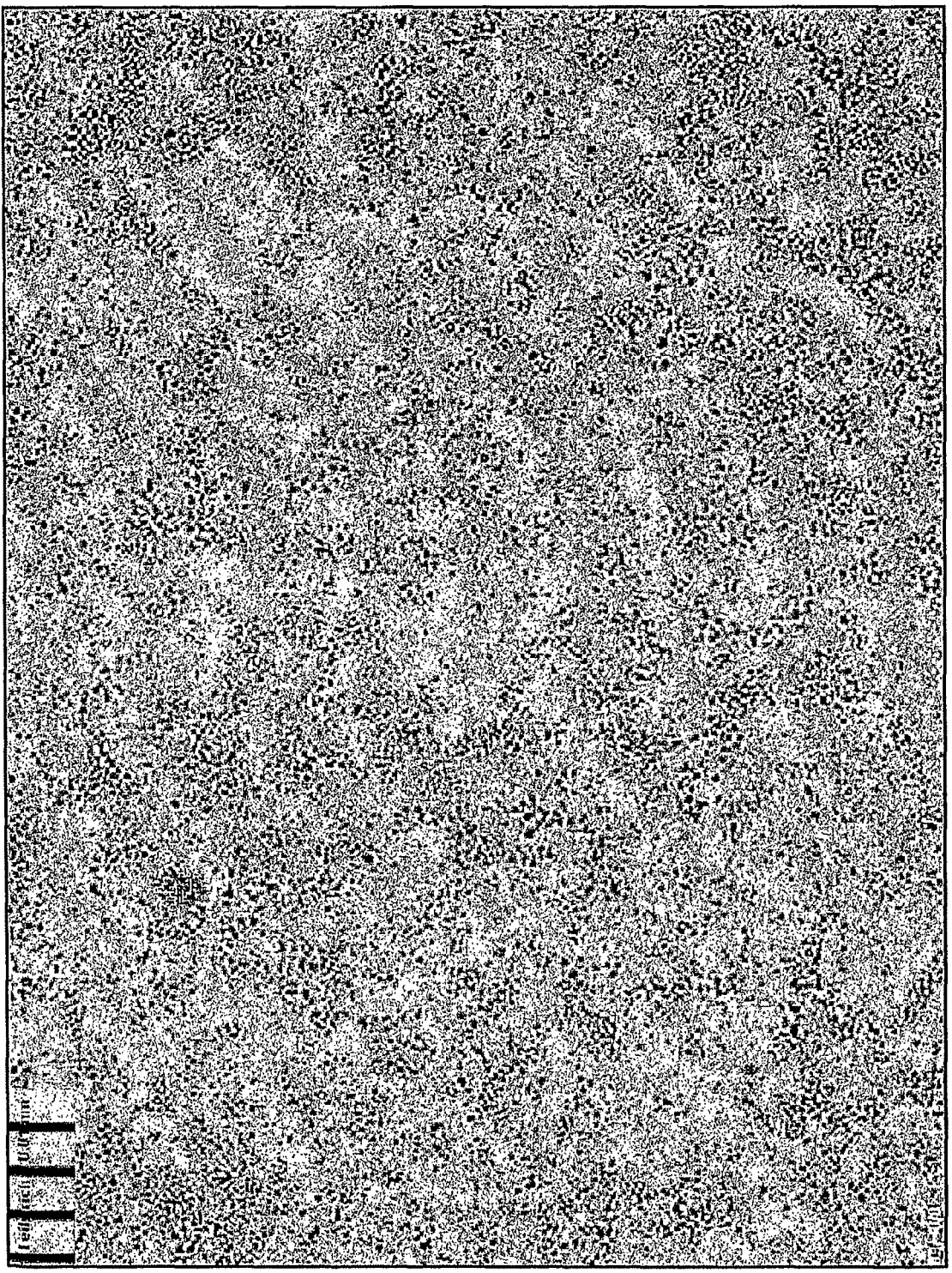

FIG. 2 relates to a microscope picture of nanoparticulate spironolactone according to the present invention after 7 months storage at room temperature. The scale relates to a distance between each bar of 0.01 mm.

Figure 3:
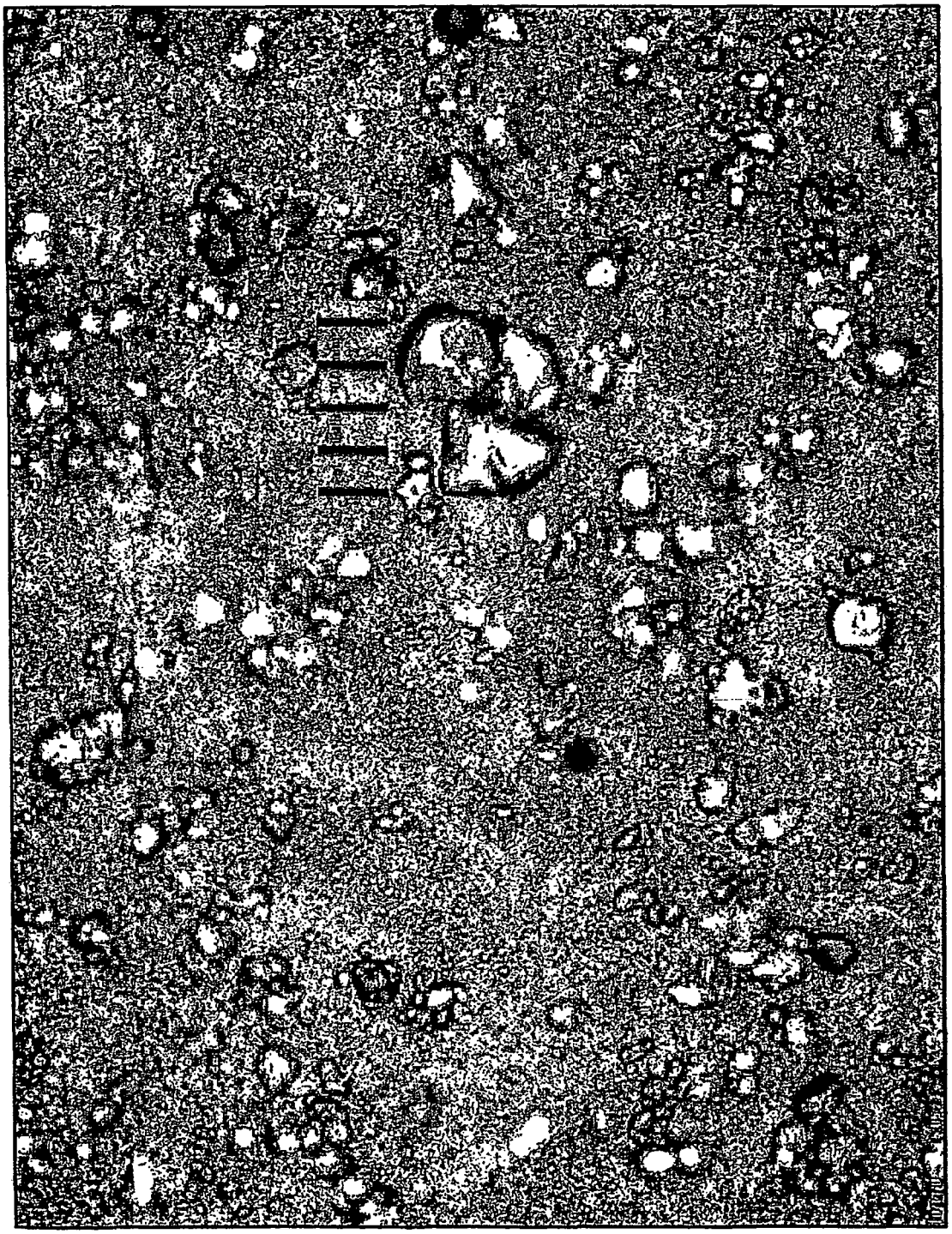

FIG. 3 relates to a microscope picture of commercially available spironolactone in non-nanoparticulate form. The scale relates to a distance between each bar of 0.01 mm.

Figure 4:
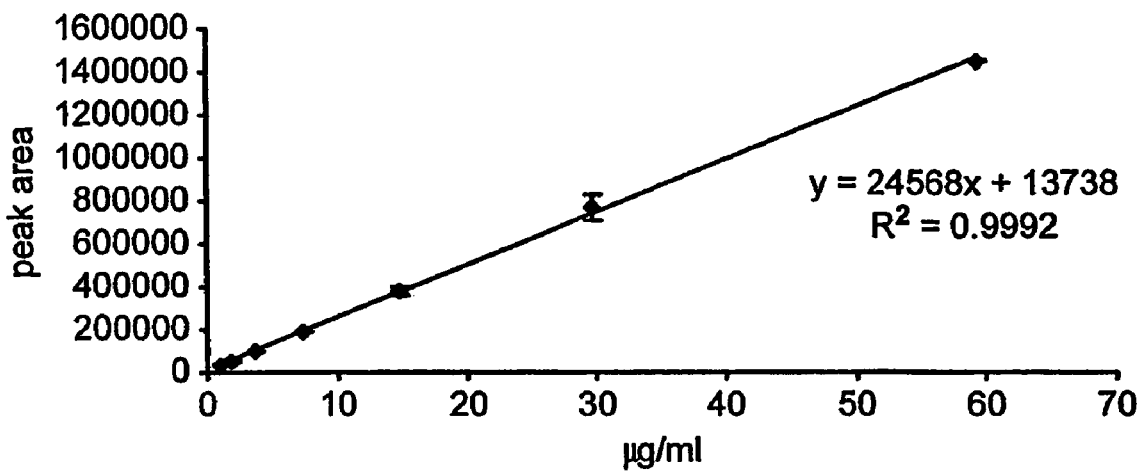

FIG. 4 relates to a typical calibration curve of Spironolactone standards of 0.93-59.2 µg/ml.

Figure 5:
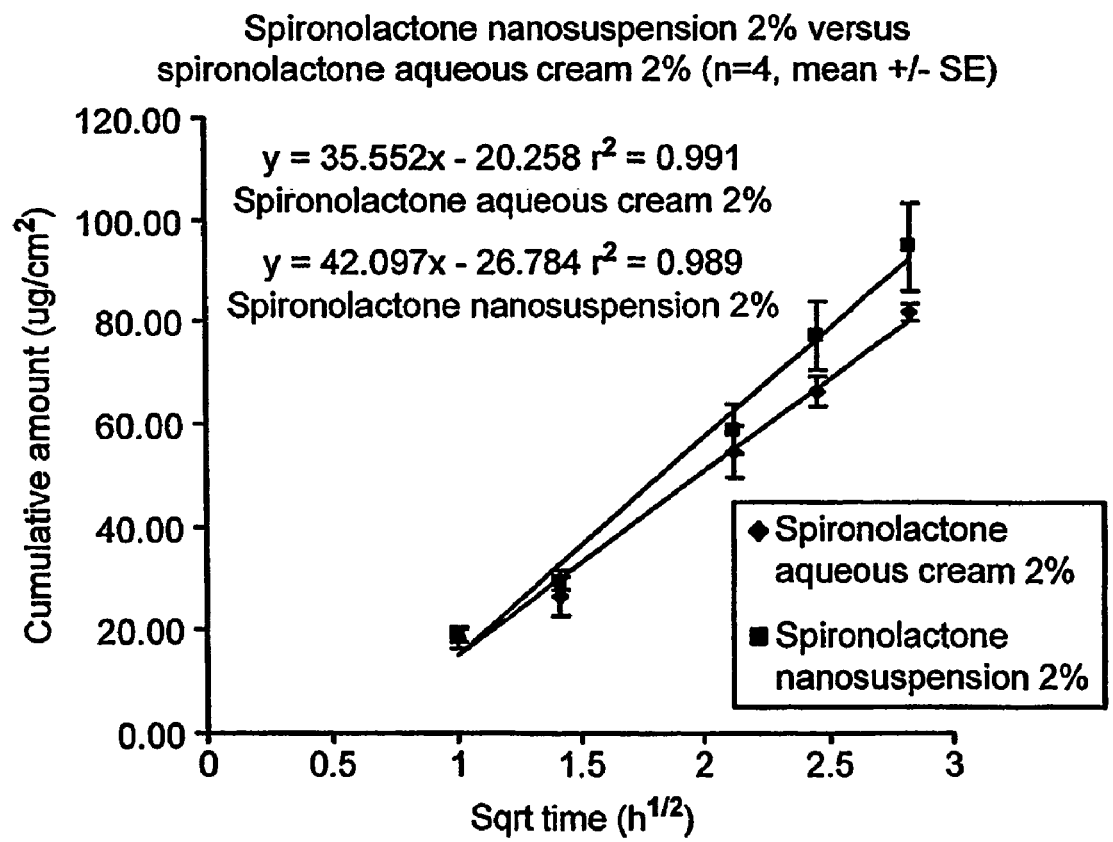

FIG. 5 relates to a graph showing the mean flux of spironolactone from the nanosuspensions (2% w/w) and aqueous cream (2% w/w) (n=4, mean±SE)

$y=35.552x-20.258$ $r2=0.991$ Spironolactone aqueous cream 2%

$y=42.097x-26.784$ $r2=0.989$ Spironolactone nanosuspension 2%

Figure 6:
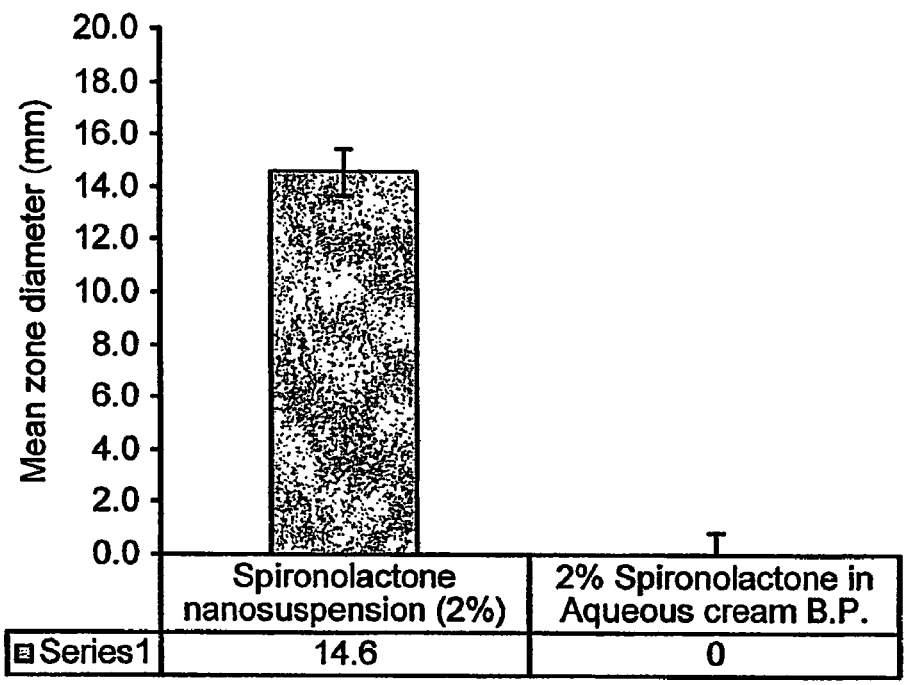

FIG. 6 relates to *S. epidermidis* mean zone diameter of Crystalip™ spironolactone formulation compared to 2% w/w spironolactone in Aqueous cream B.P. (mean±S.D.; n=5)

Figure 7:
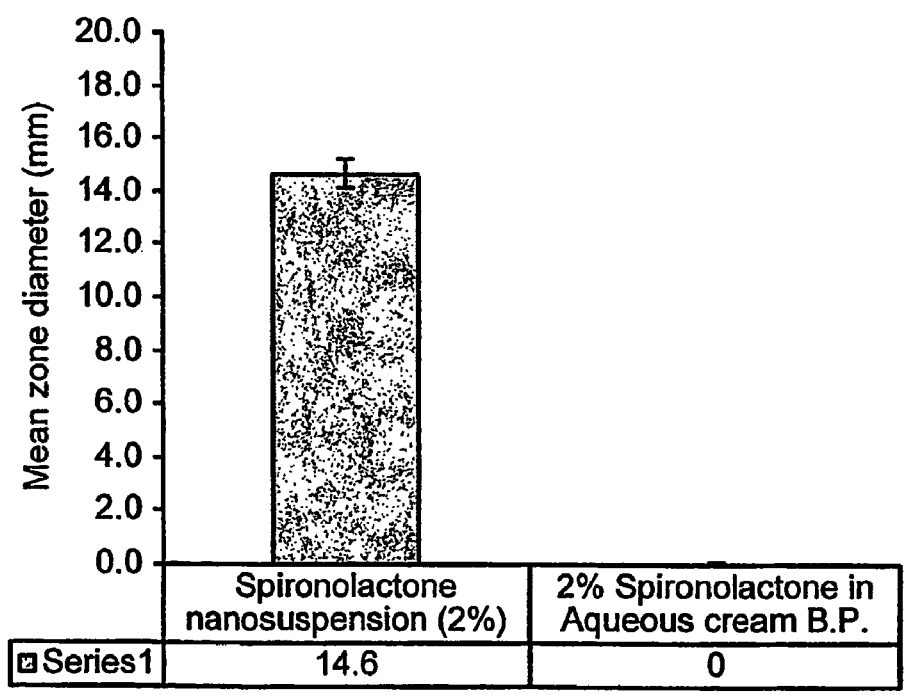

FIG. 7 relates to *P. acnes* mean zone diameter of Crystalip™ spironolactone formulation compared to 2% spironolactone w/w in Aqueous cream B.P. as comparator (mean±S.D; n=5).

Figure 8:
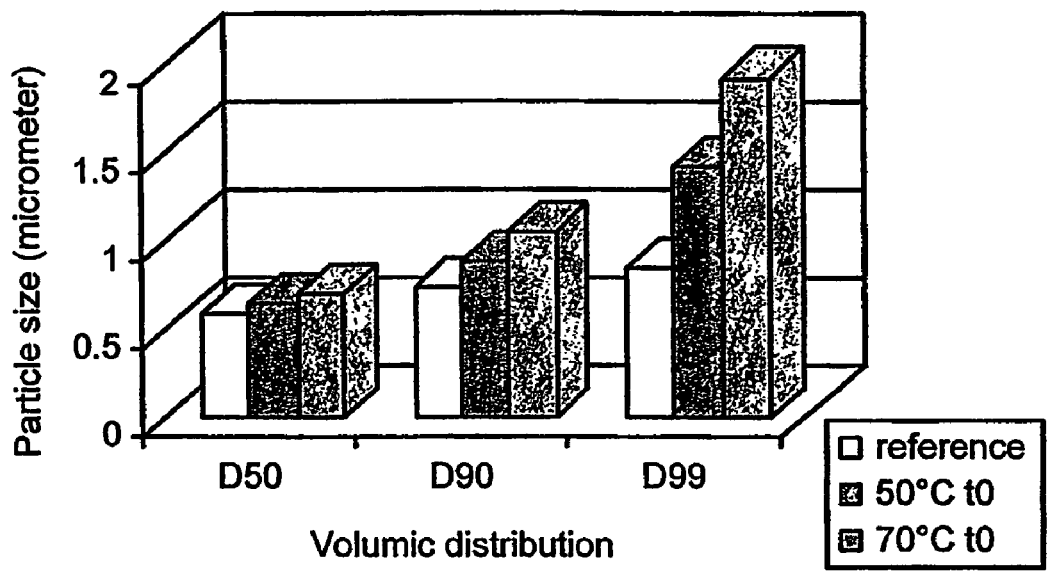

FIG. 8 relates to the particle size of spironolactone nanosuspension following heating to 50° C. (■) or 70° C.(□) then cooling compared to unheated nanosuspension (▨)

Figure 9:
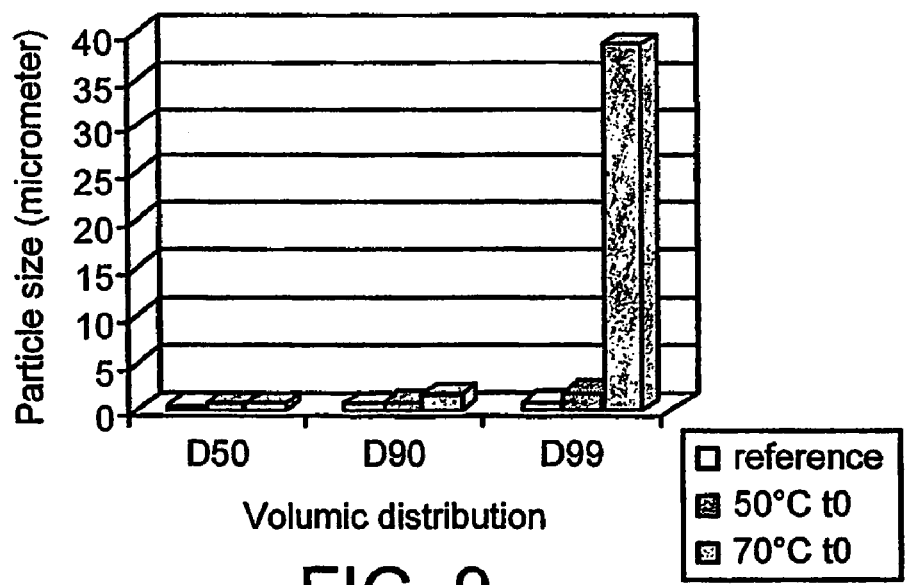

FIG. 9 relates to the particle size of spironolactone nanosuspension 24 hours after heating to 50° C. (■) or 70° C. (□) then cooling compared to unheated nanosuspension (▨)

Figure 10:
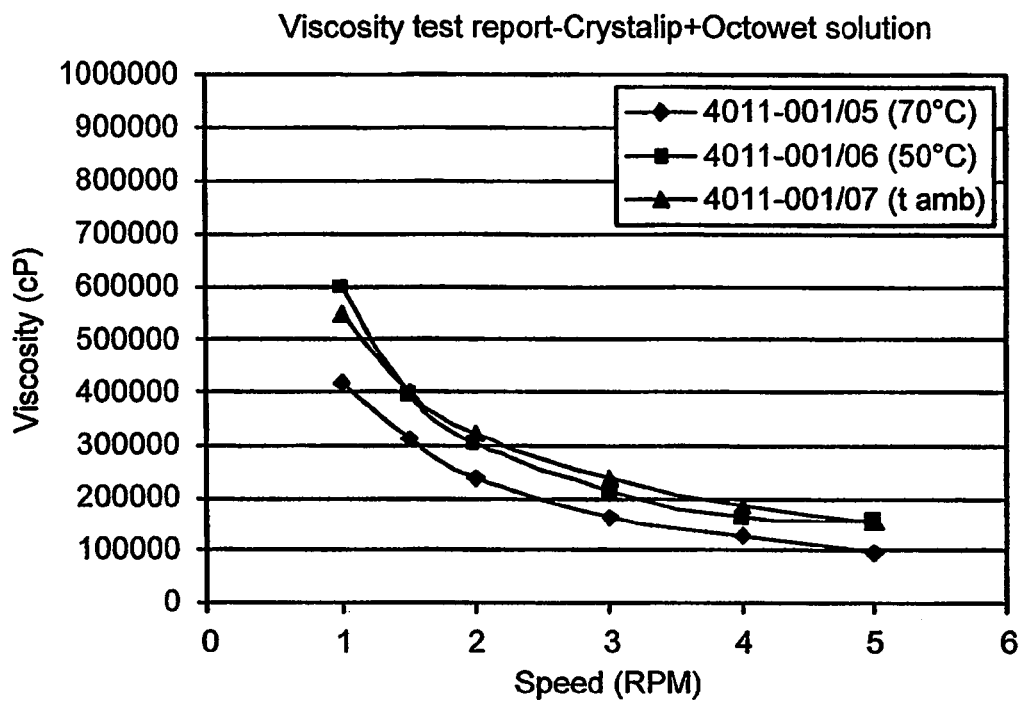

FIG. 10 relates to the viscosity of the mixture following introduction of Octowet™ at 50° C., 70° C. or room temperature.

Figure 11:
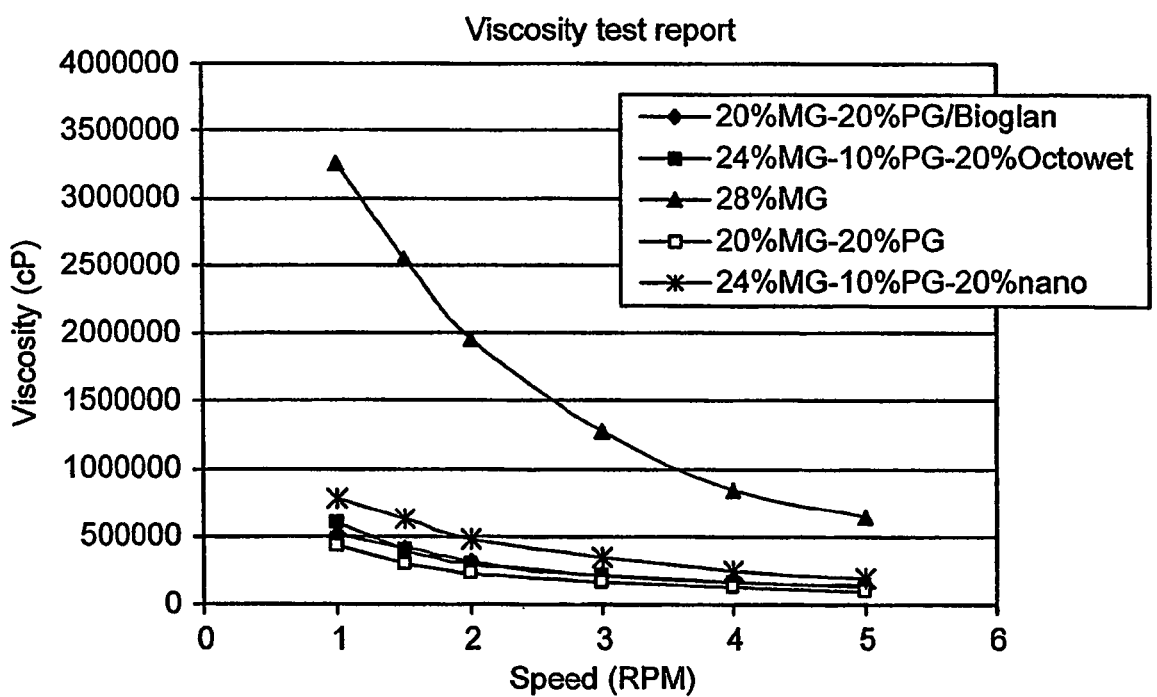

FIG. 11 relates to the effect of the composition of the mixture on its viscosity.

EXAMPLES

Example 1

Preparation of Nanoparticulate Spironolactone as a Topical Formulation

Preparation of Nanoparticulate Spironolactone.

Table 1 illustrates representative preparations of nanoparticulate spironolactone for incorporation into a crystalline structure in accordance with the present invention. The nanoparticulate spironolactone may be prepared as follows:

A preparation of an aqueous solution of the stabiliser was incorporated into water or buffer for injection under magnetic stirring until a clear solution was obtained. A slurry was formed by wetting the spironolactone with the appropriate quantity of the aqueous solution of the surfactant. The resulting suspension was dispersed using a high shear-dispersing instrument. The suspensions were left under magnetic agitation to eliminate foaming. The resulting suspensions were passed through a high-pressure piston gap homogenizer to obtain a nanosuspension. Formulations 1-7 were prepared using an Avestin C5™ and Formulations 8 and 9 were prepared using an Avestin C50™. During homogenization the drug particles are disrupted due to cavitation effects and shear forces to form small micro-and nanoparticles. The particle sizes were determined by photon correlation spectroscopy (PCS) using a Zetasizer 3000 HS™ (Malvern). $D_{50}$ and $D_{90}$ were measured by laser diffraction using a Coulter LS230.

Preparation of a Crystalip™ Composition

Table 2 illustrates representative preparations of nanoparticulate spironolactone as a topical cream, using formulations 7, 8 or 9 as shown in Table 1. The topical nanosuspension preparations were prepared as follows:

Water was heated to 70° C. and propylene glycol added. The monoglycerides were melted at 70° C., and the molten monoglycerides were then added to the water phase under stirring at 70 rpm. Cooling down of the mixture was then started. The stirring speed was increased to 95 rpm when the mixture reached around 50° C. when the viscosity increased and the cold nanosuspension added. The stirring speed was decreased to 75 rpm at 35° C. when the β-crystalline structure started to form.

TABLE 2

| | Formulation | | | |
|---|---|---|---|---|
| | A | B | C | D |
| Spironolactone Nanosuspension (formulations 7, 8 or 9 from table 1) | 20 | 10 | 20 | 20 |
| Glycerine monolaurate | 7 | 6 | 6 | 5 |
| Glycerine monomyristate | 21 | 18 | 18 | 15 |
| Propylene glycol | — | 10 | 10 | 20 |
| Water | 52 | 56 | 46 | 40 |

The following experiments were performed to determine the optimum compositions and method for producing a topical nanoparticulate spironolactone formulation in accordance with the present invention.

Selection of an Optimum Crystalip™ Composition.

Two batches of a Crystalip™ composition were produced as shown in the table below.

TABLE 1

| | Formulation | | | | | | | | |
|---|---|---|---|---|---|---|---|---|---|
| | 1 | 2 | 3 | 4 | 5 | 6 | 7 | 8 | 9 |
| Spironolactone % | 10 | 10 | 20 | 10 | 10 | 10 | 10 | 10 | 10 |
| Sodium lauryl sulphate % | 1 | — | — | 0.1 | 0.4 | 0.1 | — | — | — |
| Lutrol F68 % | — | 1 | 1 | 0.4 | 0.1 | 0.4 | — | — | — |
| Na Cl | — | — | — | — | — | 0.9 | — | — | — |
| Octowet 70 (sodium docusate) % | — | — | — | — | — | — | 0.5 (0.35) | 0.5 (0.35) | 0.5 (0.35) |
| Water | | | | QS to 100% | | | | | |
| Sample volume (ml) | 40 | 40 | 40 | 40 | 40 | 40 | 40 | 100 | 500 |
| Results | | | | | | | | | |
| $D_{50}$ (micron) | 1.69 | 0.85 | 1.06 | 0.84 | 0.88 | 0.86 | 0.78 | 0.54 | 0.539 |
| $D_{90}$ (micron) | 4.39 | 1.83 | 2.49 | 1.92 | 1.82 | 1.5 | 1.8 | 0.68 | 0.772 |
| PCS mean diameter | — | 581 | 880 | 608 | 681 | 656 | 609 | 415 | 436 |
| PI | — | 0.7 | 0.2 | 0.15 | 0.03 | 0.1 | 0.2 | 0.05 | 0.1 |

TABLE 3

Reproduction of Crystalip ™ placebo

| Batch number | Glycerine monolaurate | Glycerine monomyristate | Propylene glycol (PG) | Water |
|---|---|---|---|---|
| 4011-001/01 | 7% | 21% | / | 72% |
| 4011-001/02 | 5% | 15% | 20% | 60% |

For the first batch, a characteristic exothermic peak was seen during cooling. At the end of the cooling stage the cream was very viscous but did not have the shiny appearance typical of a β-crystalline structure. During storage, this shiny appearance started to appear.

For the second batch, an exothermic peak was not observed, however there was a shiny appearance. The viscosity seemed to be lower than the first batch.

A composition with less propylene glycol was then tested (table 4) since there were some concerns about irritation resulting from high PG concentrations. Propylene glycol is useful to retain in the composition since it may increase the antimicrobial efficacy of the base and enhance penetration of active components into the skin therefore. The following batches were manufactured:

TABLE 4

Crystalip ™ batches

| Batch number | Glycerine monolaurate | Glycerine monomyristate | Propylene glycol (PG) | Water |
|---|---|---|---|---|
| 4011-001/03 | 5% | 15% | 10% | 70% |
| 4011-001/04 | 6% | 18% | 10% | 66% |

For the batch with 20% monoglycerides (MG), viscosity dropped at around 40° C., and the mixture became liquid again just after the viscosity had started to increase.

The MG level was therefore increased to 24%. The viscosity also dropped around 40° C., but viscosity increased again during further cooling. An exothermic peak was observed at 33° C. and the final cream had a shiny appearance, which means the final β-crystalline structure had beet produced Compatibility Tests Between the Surfactant and Crystalip™.

It had previously been determined that Crystalip™ is compatible with Myrj 59 and Span 20, which are both non-ionic surfactants. However, Octowet 70PG is used for the spironolactone nanosuspension, which is an anionic surfactant. Octowet 70PG is also known as Sodium dioctyl sulfosuccinate and is a 70% solution (70% DOSS) of water and propylene glycol For a cream containing 2% spironolactone, 20% of the spironolactone nanosuspension must be incorporated since the nanosuspension contains 10% active spironolactone and 0.5% surfactant. In testing the compatibility of the Crystalip™ formulation with Octowet solution, 20% Octowet solution was therefore used and replaced part of the water phase.

The compatibility of Octowet 70PG solution with the chosen Crystalip™ formulation (10% PG+24% MG) was tested. Three batches of Crystalip™ (table 5) were manufactured in which 20% of a 0.5% Octowet 7OPG solution were introduced at different temperatures: 70° C., 50° C. and room temperature.

TABLE 5

Crystalip ™ batches including Octowet solution

| Batch number | Glycerine mono laurate | Glycerine mono myristate | Propylene glycol | Octowet solution (0.5%) | Water | T ° C.* |
|---|---|---|---|---|---|---|
| 4011-001/05 | 6% | 18% | 10% | 20% | 46% | 70 |
| 4011-001/06 | 6% | 18% | 10% | 20% | 46% | 50 |
| 4011-001/07 | 6% | 18% | 10% | 20% | 46% | room temp |

*T ° C.: temperature at which the surfactant solution has been introduced.

All three batches produced the exothermic peak and resulted in a shiny appearance. The viscosity of the batches number 05 and 06 was acceptable, but the viscosity of batch number 07 after introduction of the Octowet solution was not sufficient.

It was therefore concluded that the chosen Crystalip™ formula was compatible with 20% of a 0.5% Octowet solution. The Octowet solution was best incorporated at a temperature above the crystallisation point, rather than at room temperature.

Introduction of Spironolactone Nanosuspension in Crystalip™

The composition of the nanosuspension was 10% spironolactone and 0.5% Octowet 70PG.

Particle size of the fresh nanosuspension using laser diffraction (COULTER):D50=0.686

D90=1.033

D99=1.033

Particle size using photon correlation spectroscopy (Zetasizer 3000HS): Z average=476 nm From the compatibility tests above it was known that incorporating materials at room temperature was not a good option. It was therefore necessary to investigate heating the nanosuspension. The particle size before and after heating the suspension was measured.

The experiment was carried out as follows:

Two samples of nanosuspension were heated to 50° C. and 70° C., respectively. The temperature was held for 10 min and then the sample was cooled back to room temperature. The particle size was measured by photo correlation spectroscopy and laser diffraction at these time points:

after ultrasonication, before heating (reference)

after cooling down (t0)

after 24 h (t24 h)

TABLE 6

Determination of size particles by laser diffraction (Coulter)

| Particle size distribution | Sample identity | | | | |
|---|---|---|---|---|---|
| | Reference | 50° C. - t0 | 70° C. - t0 | 50° C. - t24 h | 70° C. - t24 h |
| D50 | 0.579 nm | 0.638 nm | 0.700 nm | 0.634 nm | 0.694 nm |
| D90 | 0.740 nm | 0.878 nm | 1.053 nm | 0.861 nm | 1.572 nm |
| D99 | 0.850 nm | 1.922 nm | 1.421 nm | 1.902 nm | 38.65 nm |

The results of Table 6 are also shown in FIGS. 8 and 9.

TABLE 7

Determination of particle size by photon correlation spectroscopy (Zetasizer 3000HS)

| Sample identity | Reference | 50° C. - t0 | 70° C. - t0 | 50° C. - t24 h | 70° C. - t24 h |
|---|---|---|---|---|---|
| Particles size (nm) | 456.3 | 469.7 | 538.3 | Not done* | Not done* |

*the size was found too large by laser diffraction measurement with PCS was not made It was shown that the results from heating the nanosuspension show a quite dramatic particle size increase for 70° C., particularly after waiting for another 24 h, which suggests some drug had gone into solution and then re-crystallised. The particle size also increased at 50° C., however there did not seem to be so much recrystallisation happening over the following 24 hours.

It was decided that a very short exposure to 50° C. would be acceptable. It was therefore concluded that the final batch should be prepared as follows:

Crystalip™ with a reduced water phase would be prepared. The nanosuspension would be sonicated, but not heated. Once the temperature of the Crystalip™ reached 50° C., the cold nanosuspension would be added, leading to a quick temperature decrease and minimisation of heat exposure of the spironolactone suspension. This process would also not interfere with Crystalip™ crystallisation, which occurs at lower temperatures.

A batch was prepared according to the above recommendation where cold nanosuspension was added to Crystalip™ at 50° C. (table 8).

TABLE 8

Crystalip ™ batches including spironolactone nanosuspension

| Batch number | Glycerine mono laurate | Glycerine mono myristate | Propylene glycol | Nano suspension | Water |
|---|---|---|---|---|---|
| 4011-001/08ac | 6% | 18% | 10% | 20% | 46% |

The batch was successful. The final cream had a good viscosity and a shiny, homogenous appearance.

Viscosity Measurement

| Sample ID | Composition |
|---|---|
| Bioglan | 20% MG-20% PG |
| 4011-001/05pc | 24% MG-10% PG-20% Octowet solution (introduce at 70° C.) |
| 4011-001/06pc | 24% MG-10% PG-20% Octowet solution (introduce at 50° C.) |
| 4011-001/07pc | 24% MG-10% PG-20% Octowet solution (introduce at room temperature) |
| 4011-001/08ac | 24% MG-10% PG-20% nanosuspension |
| 4011-001/13pc | 28% MG |
| 4011-001/17pc | 20% MG-20% PG |

The results of the viscosity results of the compositions shown in the above table are shown in FIGS. 10 and 11.

Tests with the Second Batch of Nanosuspension: 3011-05an1

As the nanosuspension was not fresh for the previous tests it was decided to make a new nanosuspension of spironolactone and to incorporate it in Crystalip™ just a few days after the manufacture. The composition of the nanosuspension used was 10% spironolactone and 0.5% Octowet 70PG. It was also investigated whether it was possible to introduce 30% of nanosuspension instead of 10% in the Crystalip™.

The particle size of the nanosuspension, just after the making, using laser diffraction was as follows: (COULTER):
D50=0.443
D90=0.657
D99=0.738

Particle size using photon correlation spectroscopy (Zetasizer 3000HS): Z average≈419.3 nm Two new batches of Crystalip™, 4014-000/01ac and 014-000/02ac were made with respectively 20% and 30% of nanosuspension in it. The process was identical to 4011-001/08ac (incorporation of the nanosuspension at 50° C. during the cooling stage). The nanosuspension was manufactured the day before the making of Crystalip™. For those two batches the pH was adjusted to the same as the market cream (Spiroderm 5% with a pH=4.16). The two batches are summarised in the following table.

| Batch number | Glycerine mono laurate | Glycerine mono myristate | Propylene glycol | 3011-05an1 | Water | Citric acid | Sodium Hydroxide |
|---|---|---|---|---|---|---|---|
| 4014-000/01ac | 6% | 18% | 10% | 20% | 45.5% | 0.5% | Up to pH = 4.16 |
| 4014-000/02ac | 6% | 18% | 10% | 30% | 35.5% | 0.5% | Up to pH = 4.16 |

The two creams were shiny but the second one 4014-000/02ac seemed to have a higher viscosity. As the nanosuspension is introduced cold, the viscosity increases more quickly for the batch with 30% of nanosuspension. Moreover the batch with 30% of nanosuspension seemed to be less homogeneous because of the increase of the viscosity.

The pH and the density of those batches were measured the next day after manufacturing, as shown in the table below.

| Batch number | pH | Density (g/cm3) |
|---|---|---|
| 4014-000/01ac | 4.29 | 0.989 |
| 4014-000/02ac | 4.22 | 0.984 |

Example 2

Size of Spironolactone Particles Before and After Storage

FIGS. 1, 2, and 3 show microscope pictures of Spironolactone according to the invention immediately after preparation, after 7 months storage and their comparison to a commercial Spironolactone. The figures contain a scale which relates to a distance between each vertical bar of 0.01 mm or 10 micrometers.

The particles shown in FIGS. 1 and 2 are almost too small to see in the light microscope. There is no particle growth over 7 months storage. In contrast, the commercial spironolactone "Spiroderm" (FIG. 3) has Spironolactone crystals present of up to 20 micrometers in size.

Example 3

Flux Studies

The flux through artificial membranes of spironolactone (2%) from a nanosuspension formulation incorporated into "Crystalip™" matrix was measured in a Franz cell set-up and compared with 2% w/w spironolactone in Aqueous cream B.P. as a comparator.

| Material | Supplier |
|---|---|
| Crystalip ™ spironolactone nanosuspension 2% Lot no. 4014-000/06atc | SkyePharma, Switzerland |
| Spironolactone Lot no. 510/0 | |
| Aqueous cream B.P. Lot no. 28076 | Hillcross, UK |
| Ethanol AnalaR grade | VWR International Ltd., UK |
| Sodium dihydrogen phosphate dihydrate Lot no. L298 | Merckeurolab |
| Deionised water | Elga Ltd., UK |
| Acetonitrile HPLC grade | Rathburns Chemicals Ltd., UK |
| Regenerated cellulose Membrane | NBS-Biological, UK |

Methods for Flux Studies

The Crystalip™ formulation was supplied by SkyePharma AG. A commercial Spironolactone comparator was not available any more at the time of the experiments. Therefore a comparator in a standard cream matrix was prepared as follows. Briefly, 100 mg of Spironolactone powder was accurately weighed and mixed with 4.90 g Aqueous cream B.P. in order to obtain a 2% w/w non-nanoparticulate spironolactone in Aqueous cream formulation.

In-vitro Diffusion Studies

Ethanol: Phosphate 'buffer' (20:80 v/v, pH 4.5) was used as the receiver fluid in order to maintain stability of spironolactone and sink conditions. The artificial membrane used was regenerated cellulose membrane.

Franz Cell Diffusion Studies

Individually calibrated Franz diffusion cells with an average diffusional surface area of 0.56±0.03 cm2 and an average receiver volume of 1.83±0.02 ml were used to conduct the diffusion experiments. The Spectra/Por® cellulose membranes were cut to appropriate size and immersed in deionised water for 30 min to remove the preservative (0.1% sodium azide), wiped with tissue to remove surface liquid and mounted onto the Franz cells. The receiver fluid was incorporated into the Franz cell, stirred constantly with a magnetic stirrer and maintained at 32° C. The membranes were allowed to equilibrate with the receiver phase for 30 min before applying the formulations. Each formulation (200 μl) was applied onto the membrane surface using a positive displacement Finnpipette®. Five sampling times were investigated (1, 2, 4, 6 and 8 h) whereby 200 μl of the receiver fluid was carefully withdrawn from the arm of the Franz cell; each sample removed was replaced by an equal volume of fresh pre warmed (32° C.) receiver fluid. Throughout the experiment, any losses in receiver fluid due to evaporation from the Franz cell were replaced to maintain a constant volume. Samples were analysed via HPLC using chromatographic conditions as follows:

| Column: | Hypersil 3 μm Phenyl BDS column (s/no. 182862) |
|---|---|
| Column length: | 150 × 4.60 mm |
| Column temperature: | 30° C. |
| Mobile phase: | 50 mM Phosphate buffer:acetonitrile (70:30 v/v) |
| Flow rate: | 1.0 ml/min |
| UV wavelength: | 238 nm |
| Injection volume: | 10 μl |
| Run time: | 15 min |

Preparation of Spironolactone Standard Curves

Spironolactone standards were prepared in receiver fluid and calibration curves were constructed in the range 0.93-59.2 μg/ml. Calibration curves with r2>0.999 were considered acceptable and a typical curve is illustrated in FIG. 4.

Data Analysis

The amount of spironolactone in the receiver fluid was corrected for sample removal. The cumulative amount of spironolactone permeated per unit membrane surface was plotted against the square root of time and the slope of the linear portion of the graph was estimated as the steady state flux. A Student's t-test was employed to statistically determine any significant difference in release of spironolactone from the 2% spironolactone nanosuspensions and 2% spironolactone Aqueous cream.

Results

FIG. 5 shows a graphical representation of the mean cumulative amount of spironolactone permeated per unit area (μg/cm2) from the two spironolactone formulations. These profiles show steady state flux for both formulations. The release rate of spironolactone from the spironolactone nanosuspension (2% w/w) was shown to be significantly faster than the aqueous cream formulation (p=0.08).

Example 4

Zone of Inhibition Assay

The antimicrobial action of two spironolactone formulations, namely spironolactone nanosuspension 2% w/w and spironolactone coarse 2% wlw, and their respective placebos were compared. A 2% w/w spironolactone in Aqueous cream B.P. formulation (in-house) was used as a comparator. The following materials were used.

| Material | Supplier |
|---|---|
| *Staphylococcus epidermidis* (ATCC 12228) | Oxoid Ltd, UK. |
| *Pseudomonas* acne (NTC 737) | Central Public Health Laboratory, UK |
| S&S Antibiotic-Assay discs(filter paper), diam ¼ inch | Aldrich Chemical company, USA |
| Aqueous cream B.P. Lot no. 28076 | Hillcross, UK |
| Spironolactone Lot no. 510/0 | SkyePharma, Switzerland |

Methods

The Crystalip™ spironolactone and placebo formulations were prepared as shown in the table below. Since a commercial Spironolactone comparator was not available any more, a comparator in a standard cream matrix was prepared as follows. Briefly, 100 mg of Spironolactone powder was accurately weighed and mixed with 4.90 g Aqueous cream B.P. to obtain a 2% w/w non-nanoparticulate spironolactone in Aqueous cream.

The batch size is 500 g, manufactured with a lab reactor IKA-LR1000.2.

| Composition | 4014-000/06atc Crystalip ™ nanosuspension 2% |
|---|---|
| MG (monoglycerides) | 24 |
| PG (propylene glycol) | 10 |
| Nanosuspension - 10% spiro | 20 |
| Spironolactone coarse | / |
| Octowet solution 0.5% w/w | / |
| Citric acid | 0.1 |
| Sodium Hydroxide up to pH | 4.16 |
| Water PPI | 45.9 |
| Physical properties | |
| pH | 4.31 |
| Density (g/ccm) | 0.900 |
| Viscosity (cP) | |
| 20 rpm | 42'327 |
| 50 rpm | 23'780 |

20±1 mg of each of the samples listed below were carefully transferred onto the surface of ¼ inch antibiotic assay discs.
1 SkyePharma AG, Crystalip™, Spironolactone nanosuspension 2% w/w 4014-000/06atc
2 2% w/w Spironolactone in Aqueous cream BP The antibiotic discs coated with each of the formulations were placed onto the surface of the organism seeded agar plates using a pair of sterile forceps.

The *S. epidermidis* plates were incubated for 24 h at 37° C.

The *P. acne* plates were incubated in the anaerobic jars and incubated for 72 h.

Zones of inhibition were measured using a pair of calipers.

Results

FIGS. 6 and 7 show the mean zone of inhibition for both formulations using seeded *S. epidermidis* and *P. acnes* plates, respectively. The Crystalip™ formulation with Spironolactone nanosuspension exhibited a considerable effect against those acne-related bacteria Aqueous cream B.P. with 2% w/w spironolactone (comparator) showed no zones of inhibition.

The base matrix therefore adds an antibacterial effect (on *S. epidermidis* and *P. acnes*) to the formulation, which is not due to the Spironolactone. The formulation does not contain any further antibiotics, or preservatives. The comparator product, which shows zero antibiotic effect on these acne-related microorganisms is preserved with phenoxyethanol. The applicants product may therefore improve acne through both the hormone activity of the drug and the antibacterial efficacy of the matrix in which it is contained.

The invention claimed is:

1. A stable topical nanoparticulate spironolactone formulation comprising nanoparticles of spironolactone incorporated into a crystalline network of polar lipids, wherein the nanoparticles of spironolactone have a mean diameter measured by photon correlation spectroscopy in the range of from about 300 nm to about 900 nm.

2. The formulation according to claim 1, comprising nanoparticles having a mean diameter, measured by photon correlation spectroscopy, in the range of from about 400 nm to about 600 nm.

3. The formulation according to claim 1, wherein the lipid has a crystallization temperature of between 20° C. and 100° C.

4. The formulation according to claim 1, wherein the crystalline network of polar lipids is formed from 13 crystals of a monoglyceride of a fatty acid having 12-18 carbon atoms, or ascorbic, phosphate or lactic esters of fatty acids or of monoglycerol ethers, or mixtures thereof.

5. The formulation according to claim 4, wherein the monoglyceride is 1-monolaurin, 1-monomyristin, 1-monopalmitin, or 1-monostearin, or a mixture of two or more thereof.

6. The formulation according to claim 1, wherein crystalline network structures of polar lipids are formed within a polar liquid.

7. The formulation according to claim 6, wherein the polar liquid is selected from water, glycerol, ethylene glycol, propylene glycol, or mixtures thereof.

8. A method of treating one or more of acne, hirsutism, androgenic alopecia, or rosacea, comprising topically applying to a subject in need thereof the nanoparticulate spironolactone formulation according to claim 1.

9. The formulation according to claim 1, wherein active drug is incorporated in the form of a nanosuspension.

10. The formulation according to claim 9, wherein the nanosuspension is an aqueous nanosuspension.

11. The formulation according to claim 10, wherein the nanosuspension comprises a stabilizer.

12. The formulation according to claim 11, wherein the stabilizer is sodium docusate.

13. A method of treating a condition that responds to anti-androgens comprising: administering a stable nanoparticulate spironolactone formulation according to claim 1 to a patient in need of such treatment, wherein said condition is acne, hirsutism, androgenic alopecia, or rosacea.

14. A process for the preparation of a stable topical nanoparticulate spironolactone formulation comprising: dispersing nanoparticulate spironolactone into a mixture of polar lipids and a polar liquid at a temperature below the transition temperature of the lipid but above the temperature at which the lipid crystalline structure is fully formed.

15. A method of treating a condition that responds to anti-androgens, comprising administering a stable topical nanoparticulate spironolactone formulation comprising nanoparticles of spironolactone incorporated into a crystalline network of polar lipids in an amount effective to treat the condition, wherein said condition is acne, hirsutism, androgenic alopecia, or rosacea, and wherein the nanoparticles of spironolactone have a mean diameter measured by photon correlation spectroscopy in the range of from about 300 nm to about 900 nm.

16. The method according to claim 8, wherein spironolactone active drug is incorporated into the formulation in the form of a nanosuspension.

17. The method according to claim 13, wherein spironolactone active drug is incorporated into the formulation in the form of a nanosuspension.

18. The formulation according to claim 1, wherein said nanoparticles do not grow following seven months in storage at room temperature.

19. The method according to claim 14, wherein said nanoparticles do not grow following seven months in storage at room temperature.

20. The method according to claim 15, wherein said nanoparticles do not grow following seven months in storage at room temperature.

* * * * *

UNITED STATES PATENT AND TRADEMARK OFFICE
CERTIFICATE OF CORRECTION

PATENT NO.         : 8,003,690 B2
APPLICATION NO.    : 10/538344
DATED              : August 23, 2011
INVENTOR(S)        : Guy Vergnault et al.

It is certified that error appears in the above-identified patent and that said Letters Patent is hereby corrected as shown below:

At column 16, claim number 4, line number 25, the phrase "talline network of polar lipids formed from 13 crystals of a.." should read --talline network of polar lipids formed from β crystals of a--.

Signed and Sealed this
Fourth Day of October, 2011

David J. Kappos
*Director of the United States Patent and Trademark Office*